United States Patent
Nelson et al.

(10) Patent No.: US 11,065,260 B1
(45) Date of Patent: Jul. 20, 2021

(54) METHOD OF TREATMENT FOR REDUCING PULMONARY INFLAMMATION IN A PATIENT WITH PATHOGEN INFECTION USING ORAL PROSTACYCLIN ANALOG DRUGS

(71) Applicants: Alan C Nelson, Gig Harbor, WA (US); Daniel J Sussman, Flagstaff, AZ (US)

(72) Inventors: Alan C Nelson, Gig Harbor, WA (US); Daniel J Sussman, Flagstaff, AZ (US)

( * ) Notice: Subject to any disclaimer, the term of this patent is extended or adjusted under 35 U.S.C. 154(b) by 0 days.

(21) Appl. No.: 16/847,449

(22) Filed: Apr. 13, 2020

(51) Int. Cl.
*A61K 31/5578* (2006.01)
*A61K 31/191* (2006.01)
*A61P 31/14* (2006.01)

(52) U.S. Cl.
CPC ........ *A61K 31/5578* (2013.01); *A61K 31/191* (2013.01); *A61P 31/14* (2018.01)

(58) Field of Classification Search
CPC .... A61K 31/5578; A61K 31/191; A61P 31/14
USPC ....................................................... 514/573
See application file for complete search history.

(56) References Cited

U.S. PATENT DOCUMENTS

| | | |
|---|---|---|
| 8,623,917 B2 | 1/2014 | Keith et al. |
| 9,381,243 B2 | 7/2016 | Johansson et al. |

FOREIGN PATENT DOCUMENTS

WO    WO-2013182683 A1 * 12/2013    ......... A61K 48/0041

OTHER PUBLICATIONS

J J F Belch et al., "Oral iloprost as a treatment for Raynaud's syndrome: a double blind multicentre placebo controlled study" Annals of the Rheumatic Diseases 1995; 54: pp. 197-200. (Year: 1995).*

Michigan Medicine, University of Michigan, "Critical care protocols for Covid-19 patients". (Year: 2020).*
Maurizio Romano et al, From Inflammation to Cancer in Inflammatory Bowel Disease: Molecular Perspectives, Anticancer Research 36: 1447-1460 (2016).
Chaolin Huang et al., Clinical features of patients infected with 2019 novel coronavirus in Wuhan, China, Lancet 2020; 395: 497-506.
J J F Belch et al., Oral iloprost as a treatment for Raynaud's syndrome: a double blind multicentre placebo controlled study, Annals of the Rheumatic Diseases 1995; 54: 197-200.
Helene Haeberle et al., Therapeutic iloprost for the treatment of acute respiratory distress syndrome (ARDS) (the ThIlo trial): a prospective, randomized, multicenter phase II study, Haeberle et al. Trials (2020) 21:242.
Marco Idzko et al., Inhaled iloprost suppresses the cardinal features of asthma via inhibition of airway dendritic cell function, J Clin Invest. 2007;117(2):464-472.
Sandra Demaria et al., Cancer and Inflammation: Promise for Biological Therapy, J Immunother. May 2010 ; 33(4): 335-351.
Hildebrand M et al., Oral iloprost in healthy volunteers, Abstract, Eicosanoids. 1991;4(3):149-54.
John E. Conour, https://www.patentdocs.org/2018/09/patenting-repurposed-drugs.html, Patenting Repurposed Drugs, Sep. 18, 2018.
Richard M. Peek, Jr. et al., Inflammation in the Genesis and Perpetuation of Cancer: Summary and Recommendations from a National Cancer Institute—Sponsored Meeting, Cancer Res 2005; 65: (19). Oct. 1, 2005.
M. Hildebrand, Pharmacokinetics and tolerability of oral iloprost in thromboangiitis obliterans patients, European Journal of Clinical Pharmacology vol. 53, Abstract (1997).

* cited by examiner

*Primary Examiner* — Joseph R Kosack
*Assistant Examiner* — Sagar Patel
(74) *Attorney, Agent, or Firm* — George A Leone; Citadel Patent Law

(57) ABSTRACT

A method of reducing mortality in a human patient with pulmonary inflammation due to coronavirus or other pathogen, the method including administering an oral dose of a prostacyclin analog drug to the patient within a therapeutic window. The prostacyclin analog drug includes oral iloprost or iloprost betadex clathrate.

2 Claims, No Drawings

METHOD OF TREATMENT FOR REDUCING PULMONARY INFLAMMATION IN A PATIENT WITH PATHOGEN INFECTION USING ORAL PROSTACYCLIN ANALOG DRUGS

TECHNICAL FIELD

The present invention relates to a method of reducing mortality in a human patient with risk of severe acute respiratory syndrome (SARS). More particularly, the invention relates to a method for reducing pulmonary inflammation in a patient presenting symptoms of or testing positive for Covid-19 infection or other coronaviruses by oral administration of a prostacyclin analog drug.

BACKGROUND

Severe acute respiratory syndrome coronavirus 2 (SARS-CoV-2), now known as Covid-19, is causing a world-wide pandemic at the time of this writing. Therapeutics are urgently needed to prevent the onset of severe disease and to reduce the risk of death of severely ill patients. Potentially effective therapeutic strategies include the use of anti-inflammatory drugs that can mitigate severe disease.

COVID-19 and Pulmonary Function

Statistics from the Chinese Centers for Disease Control and Prevention encompassing 72,314 cases reported that 81% presenting with mild symptoms resulted in an overall case fatality rate of 2.3%, and a sub-group of 5% presented with respiratory failure, septic shock and multi-organ dysfunction (China CDC Weekly). Half of the cases presenting with severe symptoms resulted in fatality. The overall death rate in the U.S., due to coronavirus, is currently approximately 3%; however, a lack of testing may overestimate this death rate. Siddiqi and Mehra (2020), physicians at Harvard Medical School, have proposed the following staging: Stage 1 (mild)—this stage involves the initial viral inoculation and early establishment of the disease where the virus multiplies and establishes residence in the host, primarily focusing on the respiratory system. Stage 2 (moderate)—pulmonary involvement (IIa) is prevalent with viral multiplication and localized inflammation in the lung. Patients develop a viral pneumonia, with cough, fever and possibly hypoxia. Stage 3 (severe)—patients develop extra-pulmonary systemic hyperinflammatory syndrome, also referred to as a cytokine storm. Inflammatory cytokines and biomarkers such as interleukin (IL)-2, IL-6, IL-7, granulocyte-colony stimulating factor, macrophage inflammatory protein 1-$\alpha$, tumor necrosis factor-$\alpha$ (TNF-$\alpha$), C-reactive protein, ferritin, and D-dimer are significantly elevated in these patients.

Treatment of COVID-19 with Anti-Inflammatory Agents

To treat COVID-19 disease, a number of agents are currently being tested in clinical trials. Several small trials employing hydroxychloroquine have given mixed results, with one showing promising results (Gautret et al., 2020) and others showing no benefit (Chen et al., 2020; Molina et al., 2020). No benefit was found in a randomized clinical trial of 199 patients treated with the antiviral agents lopinavir-ritonavir (Cao et al., 2020). Siddiqi and Mehra (2020) have suggested the possible benefit of treating COVID-19 patients with anti-inflammatory agents.

Patients infected by previous coronaviruses, severe acute respiratory syndrome (SARS) and Middle East respiratory syndrome (MERS), exhibited rapid virus replication, inflammatory cell infiltration, and cytokine storm which led to acute lung injury and acute respiratory distress syndrome (ARDS) (Channappanavar et al., 2017; Chousterman et al., 2017). Similarly, inflammation of the lungs is prevalent in COVID-19 patients, with severe cases exhibiting cytokine storm (Huang et al., 2020; Conti et al., 2020). In one study of 123 COVID-19 patients, all of them had lymphocytopenia (one of the diagnostic criteria used in China) where the remaining lymphocytes were activated (Wan et al., 2020). The percentage of CD8+ T cell reduction were 28.43% and 61.9% in mild and severe group respectively, and the NK cell reduction were 34.31% and 47.62% respectively in mildly and severely symptomatic groups.

A review of the current knowledge of anti-inflammation treatment in COVID-19 patients was published by Zhang et al. (2020). The rationale for the use of anti-inflammatory agents is to help with lung function and to prevent the often fatal lung damage that is caused by a cytokine storm. There are a variety of anti-inflammatory medications under consideration, including chloroquine/hydroxychloroquine, glucocorticoids, non-steroidal anti-inflammatory drugs, immunosuppressants, and inflammatory cytokine antagonists. Some of these, such as glucocorticoids are not recommended in the early stage of infection as they might amplify viral replication. As described in detail in the review (Zhang et al., 2020), clinical trials have shown no efficacy in treating COVID-19 patients with glucocorticoids. Additional clinical trials are underway with immunosuppressants and cytokine antagonists.

Thus, an effective method of treatment is still needed to treat coronavirus patients for reducing pulmonary inflammation, including inflammation caused by Covid-19 and other corona virus strains it's. Such a treatment is disclosed herein.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

Disclosed herein is a method of reducing mortality in a human patient with pulmonary inflammation due to coronavirus or other pathogens, the method comprising administering an oral dose of a prostacyclin analog drug to the patient within a therapeutic window.

DETAILED DESCRIPTION OF THE PREFERRED EMBODIMENTS

The following disclosure describes a method of treating pulmonary inflammation and related diseases such as pneumonia using a prostacyclin analog drug. Several features of methods and systems in accordance with example embodiments are set forth and described herein. It will be appreciated that methods in accordance with other example embodiments can include additional procedures or features different than those specifically described. Example embodiments are described herein with respect to treatment of a Covid-19 virus infection with orally administered iloprost (a prostacyclin analog). However, it will be understood that these examples are for the purpose of illustrating the principles, and that the invention is not so limited.

Definitions

Generally, as used herein, the following terms have the following meanings, unless the use in context dictates otherwise:

The use of the word "a" or "an" when used in conjunction with the term "comprising" in the claims or the specification means one or more than one, unless the context dictates otherwise. The term "about" means the stated value plus or minus the margin of error of measurement or plus or minus 10% if no method of measurement is indicated. The use of the term "or" in the claims is used to mean "and/or" unless explicitly indicated to refer to alternatives only or if the alternatives are mutually exclusive. The terms "comprise", "have", "include" and "contain" (and their variants) are open-ended linking verbs and allow the addition of other elements when used in a claim.

Reference throughout this specification, the use of "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Iloprost" as used herein is an anti-inflammation agent which comprises a synthetic analogue of prostacyclin PGI). Its formulation may include iloprost betadex clathrate.

"Object" means an individual cell, human cell, mammal cell, item, thing or other entity.

"Subject" as used herein means a human patient.

"Therapeutic window" (or "pharmaceutical window") of a drug as used herein is the range of drug dosages over time which can treat disease effectively without having toxic effects.

"Therapeutic range" of a drug as used herein is the dosage range or blood plasma or serum concentration usually expected to achieve the desired therapeutic effect. In order to maintain a patient within a defined therapeutic range, they may be subject to therapeutic drug monitoring during the therapeutic window.

In accordance with the invention herein, a prostacyclin analog drug may comprise iloprost in a form suitable for oral administration including tablets, troches, pills, capsules and the like. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, including a liquid carrier. Various other materials can be present as coatings or to otherwise modify the physical form of the dosage unit. For instance, tablets, pills, or capsules can be coated with shellac, sugar or both. A syrup or elixir can contain the prostacyclin analog, sucrose as a sweetening agent, methyl and propylparabens a preservative, a dye and flavoring such as cherry or orange flavor. Of course, any material used in preparing any dosage unit form should be pharmaceutically pure and substantially non-toxic in the amounts employed. In addition, the prostacyclin analog can be incorporated into sustained-release preparations and formulation.

Iloprost, Inflammation, and COVID-19 Treatment

Iloprost, a synthetic analogue of prostacyclin PGI2, is an excellent candidate for the treatment of COVID-19. Iloprost has been in use for decades as an effective therapeutic agent for the treatment of moderate to severe pulmonary arterial hypertension (PAH), usually in inhaled form. Perhaps the best evidence that iloprost will be an effective treatment of COVID-19 is a recently proposed Phase II clinical trial for the treatment of ARDS (Haeberle et al., 2020). In addition to its anti-inflammatory properties described below, through target-based virtual ligand screening, iloprost has been identified as a molecule with the potential to block the binding of the virus to its cellular receptor (Wu et al., 2020).

Iloprost has been shown to reduce pulmonary inflammation in several animal studies. These studies include a pressure-induced model of lung injury (Birukova et al., 2010), ischemia-reperfusion (IR) injury (Kawashima et al., 2003; Yasa et al., 2008; Erer et al., 2014 and 2016); and porcine models of ARDS (Dembinski et al., 2005; Witter et al., 2005a and 2005b). One study with human patients demonstrated that iloprost improved gas exchange in patients with pulmonary hypertension and ARDS (Sawheny et al., 2013).

There are several mechanisms by which iloprost has been shown to reduce pulmonary inflammation, including the cyclooxygenase-2 (COX-2) system with involvement of lipoxin A4 (Scully et al., 2012), Ras-related protein 1 (RAP-1) (Burkova, 2009), and IL-1β (Crutchley et al., 1994; Della Bella et al., 1997; Zor et al., 2010; Lammi et al., 2016), a critical component of lung inflammation during viral infection (Kim et al., 2015). Iloprost/prostacyclin suppresses inflammation through other pathways. Iloprost has been shown to possess anti-inflammatory and immunomodulating actions in vitro (Jores et al., 1997; Medsger et al., 1999; Czeslick et al., 2003; Zhou et al., 2007) and in vivo (Jaffar et al.; 2002; Di Renzo et al.; 2005; Zhou et al., 2007; Leibbrandt et al., 2008). Mechanisms by which iloprost reduces inflammation include its activity in reducing TNF-α production by T cells and the number of T regulatory cells, as well as in increasing IL-2 and RANKL (D'Amelio et al., 2010). In addition, iloprost has been shown to inhibit production of intracellular TNF-α and interleukin IL-6 in human monocytes (Czeslick et al., 2003).

As mentioned above, iloprost is currently used to treat pulmonary arterial hypertension (PAH), scleroderma, Raynaud's syndroma. The synthesis of iloprost was developed by the pharmaceutical company Schering AG and is marketed by Bayer Schering Pharma AG in Europe. One advantageous formulation of iloprost is iloprost betadex clathrate; an oral formulation of the drug substance iloprost currently being used in clinical trials in the field of lung cancer and lung cancer prevention, but is not commercially available. However, this particular formulation would become commercially available upon FDA approval for clinical indications such as reduction of pulmonary dysplasia and conditions precedent to that, including pulmonary inflammation.

In conclusion, an oral formulation of iloprost has been shown to have the properties required to be effective at treating COVID-19 infection, because it has been shown to be effective at inhibiting many of the pro-inflammatory molecules that result in the cytokine storm. In addition, at least theoretically, an oral formulation iloprost has the potential to block infection.

Advantages of Iloprost Over Other Drugs for Treatment of COVID-19

Unlike the other agents listed above, iloprost works through multiple pathways to inhibit pulmonary inflammation. In addition, Iloprost causes dilation of narrowed blood vessels in the lungs, decreasing pulmonary blood pressure and improving lung function. Iloprost has been used successfully for many years to treat pulmonary arterial hypertension (PAH) and Reynaud's syndrome and has no contraindications and minimal side effects.

Advantage of Oral Iloprost Over Inhaled Iloprost

The advantages of oral iloprost over the inhaled formulation (e.g., Ventavis) are based on dosing and serum levels, and on patient comfort and convenience. The half-life of inhaled iloprost is only 20 to 30 minutes. Following inhalation of iloprost (5 mcg) patients with pulmonary hypertension have iloprost peak serum levels of approximately 150 pg/mL, with Iloprost generally not detectable in the plasma 30 minutes to 1 hour after inhalation (accessdata.fda.gov). In contrast, oral iloprost is similar to infused iloprost with steady-state serum levels of 260 pg/mL (Hildebrand, 1997).

The recommended dose of inhaled iloprost is as follows: "Ventavis should be taken 6 to 9 times per day (no more than once every 2 hours) during waking hours, according to individual need and tolerability. The maximum daily dose evaluated in clinical studies was 45 mcg (5 mcg 9 times per day)." As a result of this dosing, lung and serum levels of inhaled iloprost drops to zero as the patient sleeps. Therefore, for severe PAH, the dosing is around the clock.

There are other dosing problems with inhaled medications that do not occur with oral delivery. These problems include shallow breathing in patients with respiratory disease (Kallet et al., 2007), sub-optimal use of inhalers (Price et al., 2013; Lavorini, 2013), and uneven distribution in the lungs with reduced deposition in distal regions (Berridge et al., 2000).

In general, dosing with inhaled medications can cause undesirable spiking of the drug in a patient, making it difficult to maintain a therapeutic dosage between drug dosing. Dosing orally avoids such spiking effects.

Oral Iloprost Dosage

U.S. Pat. No. 8,623,917, entitled "Uses of Prostacyclin Analogs," issued Jan. 7, 2014 to Keith et al. discloses a method for reducing a risk of developing lung cancer in a human former smoker. U.S. Pat. No. 8,623,917 (the Keith patent) is incorporated herein by reference. Although directed to treat dysplasia in subjects with high-risk for lung cancer, the Keith patent is informative with respect to dosages of iloprost that are within the therapeutic window (or pharmaceutical window) for oral iloprost. The method taught in the Keith patent comprises administering a therapeutically effective amount of prostacyclin analog comprising iloprost to the former smoker such that the risk of developing lung cancer in the former smoker is decreased by at least 10% relative to a control group with similar risk factors.

According to the Keith patent, the therapeutic dosage can generally be from about 0.1 to about 1,000 nicrograms/day, and preferably from about 10 to about 100 micrograms/day, or from about 0.1 to about. 50 micrograms/Kg of body weight per day and preferably from about 0.1 to about 20 micrograms/Kg of body weight per day and can be administered in several different dosage units. Higher dosages, on the order of about 2× to about 4×, may be required for oral administration.

In a later paper, Keith et al. found that "Following randomization, subjects were started on either iloprost or placebo at an initial dose of 1 sustained-release capsule twice daily (BID) (50 micrograms of iloprost clathrate, per capsule). The subjects had a monthly clinical evaluation and if well tolerated, iloprost or placebo was dose escalated by 1 capsule BID to a maximum dose of 3 capsules BID." (Keith et al., 2020).

In another study using oral iloprost for treatment of Raynaud's syndrome it was found that there were no serious adverse reactions or events following a protocol administering iloprost in a dosing range of 50-150 micrograms BID (Belch et al. 1995). The protocol implemented was to treat the subjects with one capsule twice on the first day. On the second day two capsules were administered BID and on the third day three capsules BID. The maximum tolerated dose was used for the remaining seven days of this study.

In another study of asymptomatic volunteers, therapeutic efficacy was shown after i.v. infusion treatment in several states of peripheral vascular disease. It was recommended that for out-patient therapy an oral dosage form should be developed. Based upon dissolution profiles and in vivo data of a pig model, three different film-coated pellet formulations were selected for pharmacokinetic characterization in nine healthy volunteers. In the first part of the study groups of three test subjects were treated with increasing dosages (150-300 micrograms) of iloprost. At 300 micrograms flushing and headache led to the discontinuation of those escalations. All formulations exhibited dose-dependent serum level profiles. The cross-over characterization in all test subjects showed that one formulation, which exhibited a modified in vitro dissolution of 60% of the dose within 1 hour in pH 7.4 phosphate buffer, was optimal from the pharmacokinetic profile. After oral administration of this formulation the bioavailable dose fraction was highest and half-maximal serum levels lasted for 2.4 hours (mean); therapeutic serum levels were maintained for 2.1-5.0 hours. This formulation was chosen for further investigation to imitate therapeutic serum level profiles as obtained after i.v. infusion for 4-6 hours with a once-a-day dosage form (Hildebrand M, et al., 1991). In one example, extrapolating from these studies, dosages for treating pulmonary inflammation due to a coronavirus strain including, for example, Covid-19, 229E (alpha), NL63 (alpha), OC43 (beta), HKU1 (beta), MERS-CoV and/or SARS-CoV may be substantially in the range of 50-150 microgram administered to a patient twice per day (BID) to remain within a therapeutic dosage. Higher dosages may be used if indicated and tolerated by the patient.

In one example, a method of reducing mortality in a human patient with pulmonary inflammation due to coronavirus or other pathogens, where the method comprises administering an oral dose of a prostacyclin analog drug to the patient within a therapeutic window.

In another example of a method of reducing mortality in a human patient with pulmonary inflammation due to coronavirus or other pathogens, the prostacyclin analog drug consists essentially of iloprost or iloprost betadex clathrate.

In another example of a method of reducing mortality in a human patient with pulmonary inflammation due to coronavirus or other pathogens, the oral dose is substantially in the range of 50-150 micrograms of iloprost or iloprost betadex clathrate administered twice daily (BID).

In another example the human patient is maintained within a defined therapeutic range while subjecting the human patient to therapeutic drug monitoring.

In another example, method of treating a human patient having a coronavirus infection in order to reduce progression of the corona virus infection in the human patient comprises determining a stage of severity of the infection in the human patient; and if the stage of severity is moderate to severe then administering an oral dose of a prostacyclin analog drug to the human patient within a therapeutic window.

In another example of a method of treating a human patient having a coronavirus infection in order to reduce progression of the corona virus infection, the prostacyclin analog drug consists essentially of oral iloprost or iloprost betadex clathrate.

In another example of a method of treating a human patient having a coronavirus infection in order to reduce progression of the corona virus infection, the oral dose is substantially in the range of 50-150 micrograms of iloprost administered twice daily (BID).

In another example of a method of treating a human patient having a coronavirus infection in order to reduce progression of the corona virus infection, the method further comprises maintaining the human patient within a defined therapeutic range and the human patient is subjected to therapeutic drug monitoring.

In another example, a method of treating a human patient having a Covid-19 virus infection in order to reduce progression of the Covid-19 virus infection in the human patient, comprises determining a stage of severity of the Covid-19 virus infection in the human patient; if the stage of severity is moderate to severe then administering an oral dose of iloprost or iloprost betadex clathrate to the human patient within a therapeutic window; wherein the oral dose of iloprost or iloprost betadex clathrate is substantially in the range of 50-150 micrograms administered twice daily (BID); and maintaining the human patient within a defined therapeutic range.

In another example, a method of treating a human patient having a Covid-19 virus infection in order to reduce progression of the Covid-19 virus disease in the human patient, the method further comprises subjecting the human patient to therapeutic drug monitoring.

In another example, a method of treating a human patient having a corona virus strain infection in order to reduce progression of a coronavirus virus strain infection in the human patient comprises determining whether the corona virus strain consists essentially of Covid-19, 229E (alpha), NL63 (alpha), OC43 (beta), HKU1 (beta), MERS-CoV or SARS-CoV; then determining a stage of severity of the corona virus infection in the human patient; if the stage of severity is moderate to severe then administering an oral dose of iloprost or iloprost betadex clathrate to the human patient within a therapeutic window; wherein the oral dose of iloprost or iloprost betadex clathrate is substantially in the range of 50-150 micrograms administered twice daily (BID); and maintaining the human patient within a defined therapeutic range.

In another example, a method of treating a human patient having a corona virus infection in order to reduce progression of a coronavirus strain virus disease in the human patient further comprises subjecting the human patient to therapeutic drug monitoring.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The teachings of the following references are incorporated herein by reference:

Belch et al. Oral iloprost as a treatment for Raynaud's syndrome; a double blind multicenter placebo controlled study. Annals of the Rheumatic Diseases, 1995, 54:197-200.

Berridge M S, Lee Z, and Heald D L. Pulmonary Distribution and Kinetics of Inhaled [11C]Triamcinolone Acetonide. J Nucl Med Oct. 1, 2000 vol. 41 no. 10 1603-1611.

Birukova A A, Fu P, Xing J, Birukov K G. Rap1 mediates protective effects of iloprost against ventilator-induced lung injury. J Appl Physiol. 2009; 107(6):1900-10.

Birukova A A, Fu P, Xing J, Cokic I, Birukov K G. Lung endothelial barrier protection by iloprost in the 2-hit models of ventilator-induced lung injury (VILI) involves inhibition of Rho signaling. Transl Res. 2010; 155(1):44-54.

Cao, B, Wang, Y, Wen, D et al. A Trial of Lopinavir-Ritonavir in Adults Hospitalized with Severe Covid-19. NEJM. 2020; doi.org/10.1056/NEJMoa2001282

Channappanavar R., Perlman S. Pathogenic human coronavirus infections: causes and consequences of cytokine storm and immunopathology. Semin. Immunopathol. 2017; 39:529-539.

Chen Jun, Liu Danping, Liu Li, Liu Ping, Xu Qingnian, Xia Lu, Ling Yun, Huang Dan, Song Shuli, Zhang Dandan, Qian Zhiping, Li Tao, Shen Yinzhong, Lu Hongzhou. A preliminary study of hydroxychloroquine sulfate in the treatment of patients with common 2019 coronavirus disease (COVID-19). Journal of Zhejiang University (Medical Edition) [J], 2020, 49 (1): 0-0 doi: 10.3785/j.issn.1008-9292.2020.

China CDC Weekly. Novel Coronavirus Pneumonia Emergency Response Epidemiology Team. The Epidemiological Characteristics of an Outbreak of 2019 Novel Coronavirus Diseases (COVID-19)—China, 2020. Published Feb. 1, 2020 http://weekly.chinacdc.cn/en/article; Date accessed: Mar. 16, 2020.

Chousterman B. G., Swirski F. K., Weber G. F. Cytokine storm and sepsis disease pathogenesis. Semin. Immunopathol. 2017; 39:517-528.

Conti P., Ronconi G., Caraffa A., Gallenga C. E., Ross R., Frydas I. Induction of pro-inflammatory cytokines (IL-1 and IL-6) and lung inflammation by Coronavirus-19 (COVID-19 or SARS-CoV-2): anti-inflammatory strategies. J. Biol. Regul. Homeost. Agents. 2020; 34.

Crutchley D J, Conanan L B, Que B G. Effects of prostacyclin analogs on the synthesis of tissue factor, tumor necrosis factor-alpha and interleukin-1 beta in human monocytic THP-1 cells. J Pharmacol Exp Ther. 1994 October; 271(1):446-51.

Czeslick E G, Simm A, Grond S, Silber R E, Sablotzki A. Inhibition of intracellular tumour necrosis factor (TNF)-alpha and interleukin (IL)-6 production in human monocytes by iloprost. Eur J Clin Invest. 2003; 33:1013-7.

D'Amelio P, Cristofaro M A, D'Amico L, Veneziano L, Roato I, Sassi F, Bisignano G, Saracco M, Pellerito R, Patanè S, Ferracini R, Pescarmona G P, Isaia G C. Iloprost modulates the immune response in systemic sclerosis. BMC Immunol. 2010 Dec. 15; 11:62.

Della Bella S, Molteni M, Mascagni B, Zulian C, Compasso S, Scorza R. Cytokine production in scleroderma patients: effects of therapy with either iloprost or nifedipine. Clin Exp Rheumatol. 1997 March-April; 15(2):135-41.

Dembinski R, Brackhahn W, Henzler D, Rott A, Bensberg R, Kuhlen R, et al. Cardiopulmonary effects of iloprost in experimental acute lung injury. Eur Respir J. 2005; 25(1): 81-7.

Di Renzo M, Pieragalli D, Meini S, De Franco V, Pompella G, Auteri A, Pasqui A L. Iloprost treatment reduces TNF-alpha production and TNF-RII expression in critical limb ischemia patients without affecting IL6. Prostaglandins Leukot Essent Fatty Acids. 2005; 73:405-10.

Erer D, Dursun A D, Oktar G L, Iriz E, Zor M H, Elmas C, et al. The effects of iloprost on lung injury induced by skeletal muscle ischemia-reperfusion. Bratisl Lek Listy. 2014; 115(7):405-10.

Erer D, Ozer A, Demirtas H, Gonul I I, Kara H, Arpaci H, et al. Effects of alprostadil and iloprost on renal, lung, and skeletal muscle injury following hindlimb ischemia-reperfusion injury in rats. Drug Des Devel Ther. 2016; 10: 2651-8.

Gautret P, Lagier J C, Parola P, Hoang V T, Meddeb L, Mailhe M, Doudier B, Courjon J, Giordanengo V, Vieira V E, Dupont H T, Honoré S, Colson P, Chabrière E, La Scola B, Rolain J M, Brouqui P, Raoult D. Hydroxychloroquine and azithromycin as a treatment of COVID-19: results of an open-label non-randomized clinical trial. Int J Antimicrob Agents. 2020 Mar. 20:105949. doi: 10.1016/j.ijantimicag.2020.105949.

Haeberle H, Prohaska S, Martus P, Straub A, Zarbock A, Marx G, Zago M, Giera M, Koeppen M, Rosenberger P. Therapeutic iloprost for the treatment of acute respiratory distress syndrome (ARDS) (the ThIlo trial): a prospective, randomized, multicenter phase II study. Trials. 2020 Mar. 4; 21(1):242. doi: 10.1186/s13063-020-4163-0.

Hildebrand M, Pfeffer M, Mahler M, Staks T, Windt-Hanke F, Schütt A. Oral iloprost in healthy volunteers. Eicosanoids. 1991; 4(3):149-54.

Hildebrand M Pharmacokinetics and tolerability of oral iloprost in thromboangiitis obliterans patients. Eur J Clin Pharmacol. 1997; 53(1):51-6.

Huang C., Wang Y., Li X., Ren L., Zhao J., Hu Y. Clinical features of patients infected with 2019 novel coronavirus in Wuhan, China. Lancet. 2020; 395:497-506.

Jaffar Z, Wan K S, Roberts K. A key role for prostaglandin 12 in limiting lung mucosal Th2, but not Th1, responses to inhaled allergen. J Immunol. 2002; 169:5997-6004.

Jorres A, Dinter H, Topley N, Gahl G M, Frei U, Scholz P. Inhibition of tumour necrosis factor production in endotoxin-stimulated human mononuclear leukocytes by the prostacyclin analogue iloprost: cellular mechanisms. Cytokine. 1997; 9:119-25.

Kallet R H, Hemphill J C 3rd, Dicker R A, Alonso J A, Campbell A R, Mackersie R C, Katz J A. The spontaneous breathing pattern and work of breathing of patients with acute respiratory distress syndrome and acute lung injury. Respir Care. 2007 August; 52(8):989-95.

Kawashima M, Nakamura T, Schneider S, Vollmar B, Lausberg H F, Bauer M, et al. Iloprost ameliorates post-ischemic lung reperfusion injury and maintains an appropriate pulmonary ET-1 balance. J Heart Lung Transplant. 2003; 22(7):794-801.

Keith et al. Oral Iloprost Improves Endobronchial Dysplasia in Former Smokers, Cancer Prev Res; 4(6) June 2011, 793-802.

Kim K S, Jung H, Shin I K, Choi B R, Kim D H. Induction of interleukin-1 beta (IL-1β) is a critical component of lung inflammation during influenza A (H1N1) virus infection. J Med Virol. 2015 July; 87(7):1104-12. doi: 10.1002/jmv.24138.

Lammi M R, Ghonim M A, Pyakurel K, Naura A S, Ibba S V, Davis C J, Okpechi S C, Happel K I, deBoisblanc B P, Shellito J, Boulares A H. Treatment with intranasal iloprost reduces disease manifestations in a murine model of previously established COPD. Am J Physiol Lung Cell Mol Physiol. 2016 Apr. 1; 310(7):L630-8.

Lavorini F. The challenge of delivering therapeutic aerosols to asthma patients. ISRN Allergy. 2013 Aug. 5; 2013: 102418. doi: 10.1155/2013/102418. eCollection 2013.

Leibbrandt A, Penninger J M. RANK/RANKL: regulators of immune responses and bone physiology. Ann N Y Acad Sci. 2008; 1143:123-50.

Medsger T A, Silman A J, Steen V D, Black C M, Akesson A, Bacon P A, Harris C A, Jablonska S, Jayson M I, Jimenez S A, Krieg T, Leroy E C, Maddison P J, Russell M L, Schachter R K, Wollheim F A, Zacharaie H. A disease severity scale for systemic sclerosis: development and testing. J Rheumatol. 1999; 26:2159-67.

Molina J M, Delaugerre C, Goff J L, Mela-Lima B, Ponscarme D, Goldwirt L, de Castro N. No Evidence of Rapid Antiviral Clearance or Clinical Benefit with the Combination of Hydroxychloroquine and Azithromycin in Patients with Severe COVID-19 Infection. Med Mal Infect. 2020 Mar. 30. pii: 50399-077X(20)30085-8. doi: 10.1016/j.medmal.2020.03.006.

Price D, Bosnic-Anticevich S, Briggs A, Chrystyn H, Rand C, Scheuch G, Bousquet, Inhaler Error Steering Committee. Inhaler competence in asthma: common errors, barriers to use and recommended solutions. J. Respir Med. 2013 January; 107(1):37-46. doi: 10.1016/j.rmed.2012.09.017. Epub 2012 Oct. 23.

Sawheny E, Ellis A L, Kinasewitz G T. Iloprost improves gas exchange in patients with pulmonary hypertension and ARDS. Chest. 2013 July; 144(1):55-62. doi: 10.1378/chest.12-2296.

Scully M, Gang C, Condron C, Bouchier-Hayes D, Cunningham A J. Protective role of cyclooxygenase (COX)-2 in experimental lung injury: evidence of a lipoxin A4-mediated effect. J Surg Res. 2012; 175(1):176-84.

Siddiqi, H. K., and Mehra, M. R. COVID-19 Illness in Native and Immunosuppressed States: A Clinical-Therapeutic Staging Proposal, J. Heart. Lung. Transplant. (2020), DOI: 10.1016/j.healun.2020.03.012.

Wan S., Yi Q., Fan S., Lv J., Zhang X., Guo L. Characteristics of lymphocyte subsets and cytokines in peripheral blood of 123 hospitalized patients with 2019 novel coronavirus pneumonia (NCP) medRxiv. 2020.

Wittwer T, Franke U F, Fehrenbach A, Ochs M, Sandhaus T, Schuette A, et al. Donor pretreatment using the aerosolized prostacyclin analogue iloprost optimizes post-ischemic function of non-heart beating donor lungs. J Heart Lung Transplant. 2005; 24(4):371-8.

Wittwer T, Franke U F, Ochs M, Sandhaus T, Schuette A, Richter S, et al. Inhalative pre-treatment of donor lungs using the aerosolized prostacyclin analog iloprost ameliorates reperfusion injury. J Heart Lung Transplant. 2005; 24(10):1673-9.

Wu C, Liu Y, Yang Y, Zhang P, Zhong W, Wang Y, Wang Q, Xu Y, Li M, Li X, Zheng M, Chen L, Li H, Analysis of therapeutic targets for SARS-CoV-2 and discovery of potential drugs by computational methods, Acta Pharmaceutica Sinica B, doi.org/10.1016/j.apsb.2020.

Yasa H, Yakut N, Emrecan B, Ergunes K, Ortac R, Karahan N, et al. Protective effects of levosimendan and iloprost on lung injury induced by limb ischemia-reperfusion: a rabbit model. J Surg Res. 2008; 147(1):138-42.

Zhang W, Zhao Y, Zhang F, Wang Q, Li T, Liu Z, Wang J, Qin Y, Zhang X, Yan X, Zeng X, Zhang S. The use of anti-inflammatory drugs in the treatment of people with severe coronavirus disease 2019 (COVID-19): The experience of clinical immunologists from China. Clinical Immunology 2020 doi.org/10.1016/j.clim.2020.108393

Zhou W, Blackwell T S, Goleniewska K, F O'Neal J, Fitzgerald G A, Lucitt M, Breyer R M, Peebles R S Jr. Prostaglandin 12 analogs inhibit Th1 and Th2 effector cytokine production by CD4 T cells. J Leukoc Biol. 2007; 81:809-17.

Zor H M, İmren Y V, Ereer D, Oktar L, Bayram H, Benson A A. Protective effects of iloprost on cardiopulmonary bypass induced lung injury. Gazi Medical Journal 21(2): 58-63, June 2010

What is claimed is:

1. A method of treating a human patient having a corona virus strain infection in order to reduce progression of the corona virus strain infection in the human patient, the method comprising:

determining whether the corona virus strain consists essentially of Covid-19, 229E (alpha), NL63 (alpha), OC43 (beta), HKU1 (beta), MERS-CoV or SARS-CoV;

then determining a stage of severity of the corona virus infection in the human patient;

if the stage of severity is moderate to severe then administering an oral dose of iloprost or iloprost betadex clathrate to the human patient within a therapeutic window;

wherein the oral dose of iloprost or iloprost betadex clathrate is substantially in a range of 50-150 micrograms administered twice daily; and maintaining the human patient within a defined therapeutic range.

2. The method of claim 1 further comprising subjecting the human patient to therapeutic drug monitoring.

* * * * *